United States Patent [19]

Yost et al.

[11] Patent Number: 5,617,873

[45] Date of Patent: Apr. 8, 1997

[54] NON-INVASIVE METHOD AND APPARATUS FOR MONITORING INTRACRANIAL PRESSURE AND PRESSURE VOLUME INDEX IN HUMANS

[75] Inventors: William T. Yost, Newport News; John H. Cantrell, Jr., Yorktown, both of Va.

[73] Assignee: The United States of America as represented by the Administrator, of the National Aeronautics and Space Administration, Washington, D.C.

[21] Appl. No.: 449,473

[22] Filed: May 23, 1995

Related U.S. Application Data

[63] Continuation-in-part of Ser. No. 297,474, Aug. 25, 1994, abandoned.

[51] Int. Cl.$^6$ ...................................................... A61B 5/05
[52] U.S. Cl. .......................... 128/748; 128/774; 33/511; 33/512
[58] Field of Search ................... 128/748, 774; 33/511, 512

[56] References Cited

U.S. PATENT DOCUMENTS

| | | | |
|---|---|---|---|
| 3,830,233 | 8/1974 | Hill | 128/71 |
| 4,003,141 | 1/1977 | Leroy | 128/748 X |
| 4,080,653 | 3/1978 | Barnes, Jr. et al. | 128/748 X |
| 4,114,606 | 9/1978 | Seylar | 128/748 X |
| 4,122,427 | 10/1978 | Karsh | 340/1 |
| 4,124,023 | 11/1978 | Fleischmann et al. | 128/2 |
| 4,147,161 | 4/1979 | Ikebe et al. | 128/748 |
| 4,197,856 | 4/1980 | Northrop | 128/660 |
| 4,204,547 | 5/1980 | Allocca | 128/748 |
| 4,564,022 | 1/1986 | Rosenfeld et al. | 128/748 |
| 4,576,035 | 3/1986 | Hooven et al. | 128/748 X |
| 4,610,255 | 9/1986 | Shimura et al. | 128/660 |
| 4,759,375 | 7/1988 | Namekawa | 128/663 |
| 4,995,401 | 2/1991 | Bunegin et al. | 128/774 X |
| 5,117,835 | 6/1992 | Mick | 128/774 X |
| 5,191,898 | 3/1993 | Millar | 128/748 |
| 5,325,865 | 7/1994 | Beckman et al. | 128/748 |

Primary Examiner—Sam Rimell
Assistant Examiner—Robert V. Racunas
Attorney, Agent, or Firm—Kimberly A. Chasteen

[57] ABSTRACT

Non-invasive measuring devices responsive to changes in a patient's intracranial pressure (ICP) can be accurately calibrated for monitoring purposes by providing known changes in ICP by non-invasive methods, such as placing the patient on a tilting bed and calculating a change in ICP from the tilt angle and the length of the patient's cerebrospinal column, or by placing a pressurized skull cap on the patient and measuring the inflation pressure. Absolute values for the patient's pressure-volume index (PVI) and the steady state ICP can then be determined by inducing two known changes in the volume of cerebrospinal fluid while recording the corresponding changes in ICP by means of the calibrated measuring device. The two pairs of data for pressure change and volume change are entered into an equation developed from an equation describing the relationship between ICP and cerebrospinal fluid volume. PVI and steady state ICP are then determined by solving the equation. Methods for inducing known changes in cerebrospinal fluid volume are described.

9 Claims, 2 Drawing Sheets

NON-INVASIVE METHOD AND APPARATUS FOR MONITORING INTRACRANIAL PRESSURE AND PRESSURE VOLUME INDEX IN HUMANS

ORIGIN OF THE INVENTION

The invention described herein was made in the performance of work done by employees of the U.S. Government and may be manufactured and used by or for the government for governmental purposes without the payment of any royalties thereon or therefor.

This is a continuation-in-part of application Ser. No. 08/297,474 filed on Aug. 25, 1994 abandoned.

BACKGROUND OF THE INVENTION

1. Field of The invention

This invention relates in general to measuring/monitoring of intracranial pressure and pressure volume index in human patients, and more specifically to a non-invasive method for monitoring intracranial pressure and changes in intracranial pressure.

2. Description of the related art

Monitoring of intracranial pressure and pressure volume index is of significant diagnostic and post-operative importance for patients with cranial injuries, pathologies, or other conditions, that may affect the pressure of the subarachnoidal fluid around the brain, and for patients who have undergone brain surgery.

Intracranial pressure is regularly measured and monitored by means of a pressure sensor inserted through the skull into the brain. Usually a hole is drilled in the skull, and a catheter with a pressure sensor is inserted into the brain fluid. To obtain a pressure volume index, the change in intracranial pressure is monitored after a known bolus of saline solution is inserted into the cerebrospinal fluid, or after a saline solution is inserted at a known rate. This known procedure, while simple and accurate, is not suitable for long term monitoring, because an open wound must be maintained in the skull for the catheter with the pressure sensor. Antibiotics are only partially effective in treating cranial infections, so the pressure sensor can only be left in situ for two weeks or less.

Long term monitoring of intracranial pressure, without the need for maintaining an open wound in the skull, is possible if a pressure sensor with a transmitter is implanted into the brain. The intracranial pressure is thereafter monitored by means of a receiver located outside the skull. Such a solution however, is unattractive because of risks involved in implanting anything in the brain, and because of the problems of providing power to an implanted transmitter. One such remote pressure sensor is described in U.S. Pat. No. 4,124,023 to Fleischmann et al. However, this device uses nuclear material as an energy source, making it poorly suited for implantation into a human brain.

Other methods, claiming to be non-invasive methods suitable for monitoring of intracranial pressure, are based on the measurement of some quantity that depends on intracranial pressure, but which does not have a fixed relationship to intracranial pressure.

One such method is described in U.S. Pat. No. 4,204,547 to Allocca. Allocca occludes the blood flow in a jugular vein for a few seconds, and measures the resulting rate of change of blood flow within the jugular vein upstream of the occlusion as an indicator of the intracranial pressure.

Another such method, proposed in U.S. Pat. No. 4,564,022 to Bosenfeld et al., directs a sensory stimulus towards the patient, e.g. a flash of light into the eyes, and measures the latency of a resulting negative-going wave of electrical brain activity as an indicator of intracranial pressure.

These known indirect methods may be used, under very restricted conditions, as possible indicators of variations of the intracranial pressure in a patient. However, absolute values for the intracranial pressure cannot be obtained directly as there is no predetermined fixed ratio between the observed signals, obtained by these known non-invasive monitoring methods, and the absolute value of the intracranial pressure. Such calibration is possible by inserting a pressure sensor into the brain of the patient being monitored, however, this is a traumatic and undesirable procedure.

SUMMARY OF THE INVENTION

Accordingly, it is the object of the present invention to provide a non-invasive method for measurement of absolute values of intracranial pressure and pressure volume index in a human patient.

It is another object of the present invention to provide a non-invasive method for long term monitoring of both intracranial pressure and the pressure volume index in a human patient.

It is a further object of the present invention to provide a non-invasive method for calibrating indirect measurements of intracranial pressure to obtain absolute values for intracranial pressure.

It is a still further object of this invention to provide a means to monitor changes in intracranial pressure in a human patient.

These and other objects of the invention are achieved by a method for non-invasive measurement of intracranial pressure and pressure volume index, which comprises the steps of: providing a non-invasive measuring device responsive to intracranial pressure, calibrating said measuring device by introducing known changes in intracranial pressure and recording the pressure changes by the measuring device, inducing known changes in the volume of the cerebrospinal fluid while measuring the corresponding changes in intracranial pressure by means of said calibrated measuring device, obtaining two sets of corresponding values for change in volume ($\Delta V$) and change in intracranial pressure ($\Delta p$), entering each of the two sets of values for $\Delta V$ and $\Delta p$ into equation $$\Delta P = P_0(10^{\frac{\Delta V}{PVI}} - 1)$$

to form a set of two equations with $P_0$ and PVI unknown, and solving said set of two equations for PVI and $P_0$ to obtain accurate values for the pressure volume index PVI and the intracranial pressure $P_0$ for the patient.

BRIEF DESCRIPTION OF THE DRAWINGS

These and other objects of the present invention will be understood from the description herein, with reference to the accompanying drawings, in which.

DETAILED DESCRIPTION OF A PREFERRED EMBODIMENT

Figure 1A:
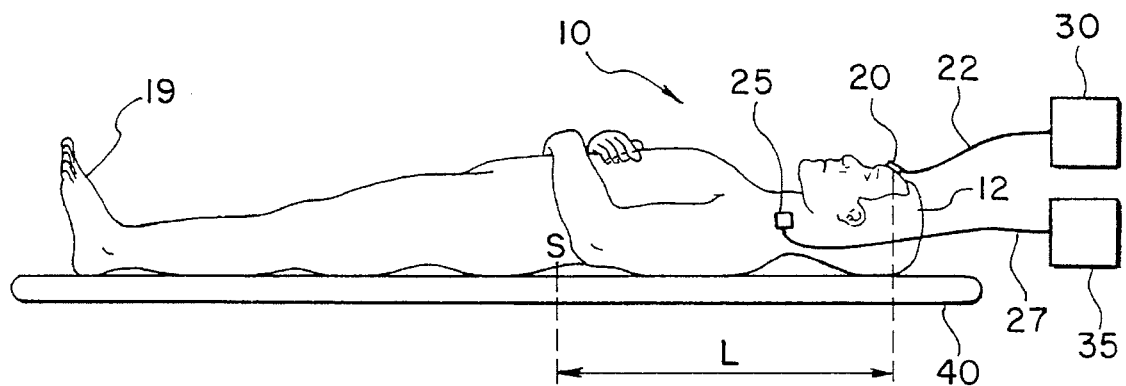
FIG. 1A is a side view of a patient with sensing devices attached to forehead and neck lying in supine position on a horizontal hospital bed.

The human brain and the spinal cord are immersed in a fluid called the cerebrospinal fluid. The cerebrospinal fluid (csf) is continuously generated and reabsorbed by the body. The csf is contained in a membrane covering the inside of the skull and the spinal cord, having a sack at the sacrum. The brain and the membrane containing the csf also contain blood vessels, which are in direct communication with the csf and add to the total volume of the cerebrospinal system. The blood volume varies rhythmically with the heart beat, causing corresponding oscillations in the intracranial pressure (ICP). An accurate regulating process in the brain normally controls the generation process, the reabsorption process and the blood volume in the brain to maintain a constant ICP average value of about 40 $mm_{Hg}$. However, the regulating process can be disturbed, e.g. by tumors in the brain, or by trauma to the brain, causing the ICP change. As little as 10 $mm_{Hg}$ increase above average value in the ICP may cause insidious damage to the brain.

When the ICP varies, the total volume of the csf also varies. As an example a relationship between volume and ICP is expressed by equation (1) for the cerebrospinal system for small values of $(V-V_0)$.

$$P = P_0 \times 10^{\frac{V-V_0}{PVI}} \qquad (1)$$

where:

P=peak ICP

V=csf volume associated with P $P_0$=Steady state reference pressure for ICP $V_0$=Steady state reference volume of csf corresponding to $P_0$ PVI=Pressure-Volume Index PVI is a constant that depends on pathological conditions of a given patient and varies from patient to patient, such that no fixed or predetermined value for PVI can be used in equation (1). An accurate value for PVI can, however, be calculated from known values for changes in ICP ($\Delta p$) and volume ($\Delta V$) as follows:

Subtracting $P_0$ from each side of equation (1) gives equation (2):

$$\Delta P = P_0(10^{\Delta V/PVI} - 1) \qquad (2)$$

where $\Delta V = V - V_0$ = small variation in volume from $V_0$ $\Delta P = P - P_0$ = small variation in pressure from $P_0$ If two pairs of $\Delta V$ and $\Delta P$ are measured, equations (3a) and (3b) are obtained:

$$\Delta P_1 = P_0(10^{\Delta V_1/PVI} - 1) \qquad (3a)$$

$$\Delta P_2 = P_0(10^{\Delta V_2/PVI} - 1) \qquad (3b)$$

Equations (3a) and (3b) are a set of two equations with only two unknown variables, PVI and $P_0$, so PVI and $P_0$ can be calculated by solving the simultaneous equations (3a) and (3b) by known methods. Examples of methods for solving this set of equations are given below.

By taking the ratio of equations (3a) and (3b), equation (4) is obtained:

$$\frac{\Delta P_1}{\Delta P_2} = \frac{10^{\Delta V_1/PVI} - 1}{10^{\Delta V_2/PVI} - 1} \qquad (4)$$

A quite accurate value for PVI is obtained by inserting into equation (4) data from the measurement of two pairs of corresponding values for $\Delta V$ and $\Delta p$ and fitting a computer generated algorithm of equation (4) to the data by varying PVI, or by using the "SOLVE" function in modern scientific calculators.

An approximate, but quite accurate, value for PVI may also be obtained by expanding the exponential functions in the numerator and the denominator of the right hand side of equation (4) in a truncated power series, collecting terms, and solving the resulting equation for PVI. If the first three terms in the power series is kept, equation (5) for PVI is obtained:

$$PVI = \frac{\frac{\Delta P_1}{\Delta P_2}(\Delta V_2)^2 - (\Delta V_1)^2}{0.868\left[\Delta V_1 - \frac{\Delta P_1}{\Delta P_2}\Delta V_2\right]} \qquad (5)$$

If the first four terms in the power series is kept, the more accurate, but still approximate, equation (6) for PVI is obtained:

$$PVI = A/B \qquad (6a)$$

Where:

$$A = 4.61\left[\frac{\Delta P_1}{\Delta P_2}(\Delta V_2)^3 - (\Delta V_1)^3\right] \qquad (6b)$$

and:

$$B = 3\left[(\Delta V_1)^2 - \frac{\Delta P_1}{\Delta P_2}(\Delta V_2)^2\right] + \left[24\frac{\Delta P_1}{\Delta P_2}(\Delta V_1)^3(\Delta V_2) + 24\frac{\Delta P_1}{\Delta P_2}(\Delta V_2)^3(\Delta V_1) - 18\frac{\Delta P_1}{\Delta P_2}(\Delta V_1)^2(\Delta V_2)^2 - 15\left(\frac{\Delta P_1}{\Delta P_2}\right)(\Delta V_2)^4 - 15(\Delta V_1)^4\right]^{1/2} \qquad (6c)$$

Once PVI is obtained, $P_0$ can be calculated from either of equations (3a) or (3b) by inserting the correct value for PVI.

Another way to calculate $P_0$ from a single measured pair of $\Delta P$ and $\Delta V$ when PVI has been determined may also be obtained by taking the derivative of equation (1) to get equation (7):

$$\frac{dP}{dV} = \frac{P_0}{0.434(PVI)} 10^{\frac{\Delta V}{PVI}} \qquad (7)$$

For small variations in P and V, dP and dV can be replaced by $\Delta p$ and $\Delta V$, respectively, and the resulting equation solved to get an approximate, but quite accurate equation (8) for $P_0$:

$$P_0 = 0.434(PVI)\frac{\Delta P}{\Delta V} 10^{\frac{-\Delta V}{PVI}} \qquad (8)$$

Measurements of $\Delta P$ and $\Delta V$ can be obtained by non-invasive methods. Two preferred methods, but by no means the only methods, to measure $\Delta P$ and $\Delta V$ for the determination of intracranial pressure and pressure-volume index will be described below.

It is commonly assumed that the skull of an adult is so rigid that the skull volume is constant. It is therefore assumed that changes in csf volume (ΔV) involve mainly compression of the spongy brain tissue. Comprehensive tests have shown that this assumption is incorrect. The skulls of adults actually expand and contract like balloons with changes in ICP, and this expansion and contraction of the skull accounts for almost all of the volume changes in the csf caused by variations in the ICP.

Any measurement system or device sufficiently sensitive to respond to appropriate anatomical configuration changes caused by pressure changes can accordingly be used to measure changes in ICP. A preferred device for measuring small variations in skull size in response to variations in ICP is the constant frequency pulsed phase-locked-loop (CFP-PLL) ultrasonic measurement device described by U.S. Pat. No. 5,214,955 issued to Yost and Cantrell, and also described in a paper entitled *"Constant frequency pulsed phase-locked-loop instrument for measurement of ultrasonic velocity"* by Yost, Cantrell and Kushnick, published in Rev. Sci. Instrum. 62 (10) October 1991. The CFPPLL measurement device applied to measuring or monitoring intracranial pressure will be described below with reference to FIG. 4.

The signal from the ultrasonic CFPPLL device depends on the diameter of the cranium and is not a direct measure of the intracranial pressure ICP. This is true for all measurement devices based on mechanical deformation of the skull or related structures, as well as all other known non-invasive measurement devices responsive to intracranial pressure variations. The signal from such non-invasive measurement devices thus can not be used for measurements or monitoring of absolute ICP variations unless a calibration as will be described herein has first been performed.

A. Methods to measure ΔP.

1. Tilt angle method.

Figure 1B:
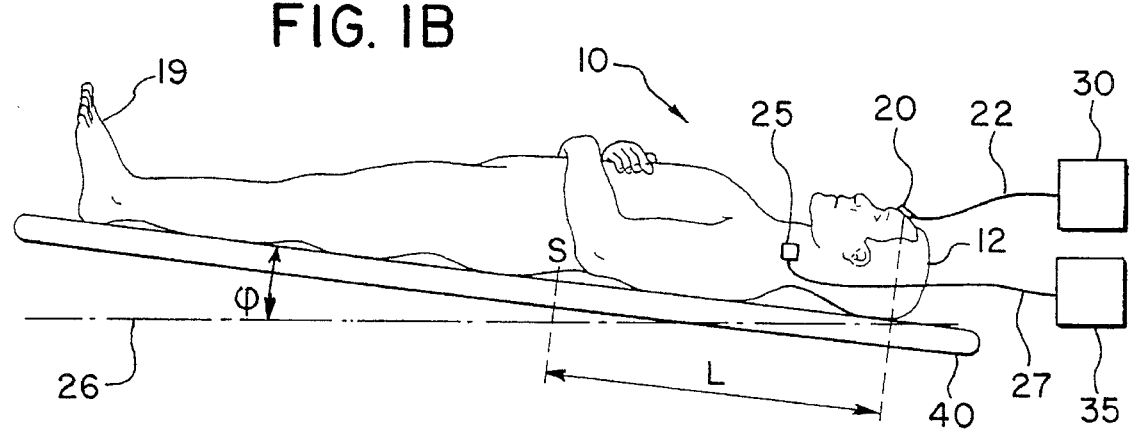
FIG. 1B is a side view of a patient with sensing devices attached to forehead and neck lying in supine position on a tilted hospital bed.

FIGS. 1A and 1B show a patient 10 lying supine on a hospital bed 40. An ultrasonic transducer 20 mounted on the front of the skull above the nose and approximately 1 cm below the hairline is connected via a cable 22 to an electronic apparatus 30. The measuring device 20, 30 provides an output proportional to changes in the travel time of an ultrasonic toneburst emitted by the transducer 20 and reflected back to the transducer 20 from the opposite side of the skull 12 or other appropriate landmark L.

In FIG. 1A the bed 40 is horizontal, and in FIG. 1B the bed 40 is tilted by an angle φ from the horizontal 26, such that the patient's legs 19 are higher than the head 12. The cerebrospinal fluid is contained in membranes extending from the inside of the top of the skull 12 to the sacrum, which lies approximately at "S" in FIGS. 1A and 1B. When the bed 40 is tilted as shown, the intracranial pressure will increase. Measuring device 20,30 provides a measurement of a change in skull 12 dimension in response to a change in intracranial pressure. If the distance from the center of the skull 12 to the sacrum is L, as indicated in FIGS. 1A and 1 B, the increase in pressure will be as given in equation (9):

$$\Delta P = \rho g L \sin \phi \quad (9)$$

where:

ΔP=Pressure change

ρ=Mass density of the spinal fluid g=Gravitational constant

L=Distance

φ=Tilt angle for patient

By using various tilt angles φ, the various changes in intracranial pressure (ICP) can be calculated from equation (9). These calculated changes in ICP can be used to calibrate the output from the measuring device 30, or any other appropriate measuring device sufficiently sensitive to respond to appropriate anatomical configuration changes caused by changes in intracranial pressure.

2. Pressurized skull cap method.

Figure 2:
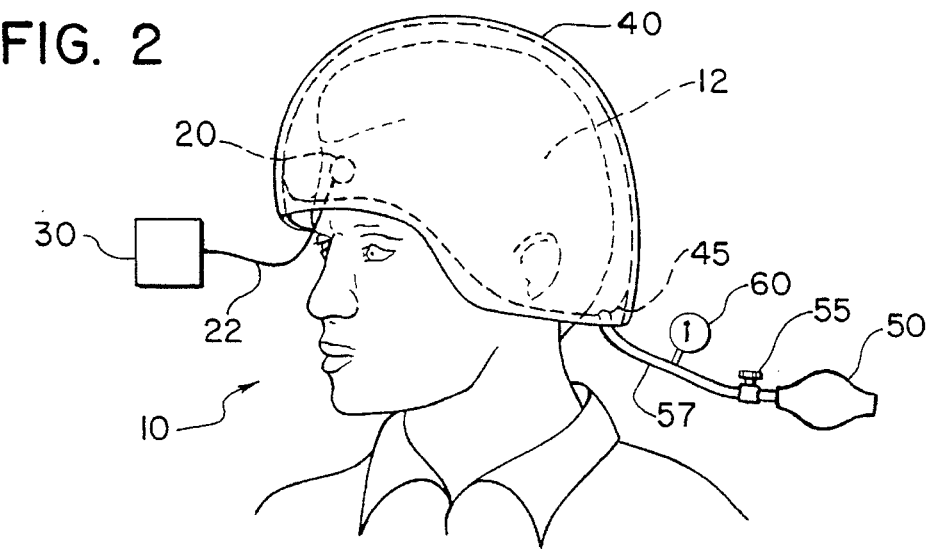
FIG. 2 is a perspective view of a seated patient with a sensing device attached to the forehead and fitted with a pressurized skull cap.

FIG. 2 illustrates another method of calibration, which uses a helmet 40 containing an inflatable skull cap 45, in which a known pressure is applied to the cranial vault 12 by means of a hose 57, a pump 50, a valve 55, and a manometer 60. Calibration is accomplished by correlating the output of a measuring device with a transducer 20 mounted on the front of the skull 12 with the applied pressure in the skull cap 45. The accuracy of this method depends on the refinements of the design of the skull cap 45 and may differ from the accuracy of the tilt-angle method outlined above.

B. Methods to vary and measure ΔV:

1. Bolus Injection method.

Figure 3:
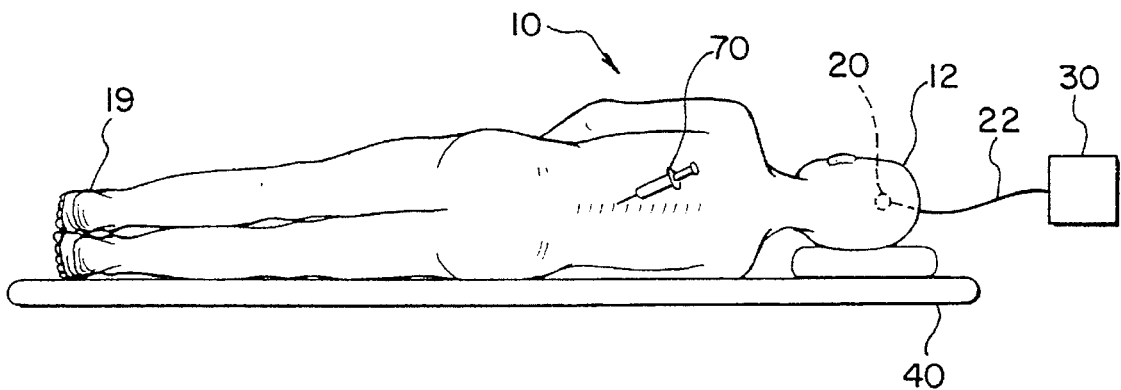
FIG. 3 is a perspective view of a patient with a sensing device attached to the forehead lying on the side.

FIG. 3 shows a patient 10, whose cerebrospinal axis is in the supine position, but where the patient is rotated onto the patient's side. The patient has an ultrasonic transducer 20 placed against the skull directly above the nose and approximately one centimeter below the hair line. This transducer 20 is connected via cable 22 to an electronic apparatus 30 for measurement of small variations in the diameter of the skull 12.

Between appropriate vertebrae, or at an other appropriate access point, a measured bolus of saline or other appropriate solution is injected by a syringe 70 into the cerebrospinal system. Let the volume of a first injection be $\Delta V_1$. By assuming that the injection of this bolus is given at the clinically recommended and appropriate injection rate, it will give rise to a peak change in intracranial pressure $\Delta P_1$. This pressure change $\Delta P_1$ is measured by readings from the measuring device 20, 30, which previously has been calibrated by the tilt angle method or the pressurized skull cap method, and is recorded along with the corresponding bolus injection volume $\Delta V_1$.

After allowing time for the intracranial pressure ICP to equilibrate to its steady state value following the first bolus injection, a second bolus injection of volume $\Delta V_2$ is given, and the resulting peak change in intracranial pressure $\Delta p_2$ is measured.

The two measured pairs of values of ΔV and Δp are then inserted into equations (3a) and (3b), and the patient's pressure-volume index PVI and the intra-cranial pressure $P_0$ is calculated by solving the two simultaneous equations by one of the methods described above in connection with equations (4)–(8).

2. Blood Flow Method:

Another method for measurement of ΔV is based on measurement of changes in blood flow to the brain, as indicated in FIG. 1A.

A patient 10 resting in supine position on a horizontal hospital bed has an ultrasonic transducer 20 placed against the front of the skull 12. The transducer 20 is connected via a cable 22 to an electronic apparatus 30 for accurate measurement of small variations in the diameter of the skull 12. The measuring device 20, 30 has previously been calibrated by the tilt angle method or the pressurized skull cap method described above to provide accurate readings of variations in the intracranial pressure.

The patient 10 also has an ultrasonic blood flow transducer 25 mounted on the neck. The blood flow transducer 25 is connected via a cable 27 to an blood flow meter 35. The blood flow transducer 25 with associated blood flow meter 35 is arranged to measure the blood flow in the patient's jugular vein. The diameter of the jugular vein can be determined by using an ultrasonic A-scan instrument. By using the determined vein diameter together with the velocity profile from the blood flow meter 35, an instantaneous blood volume change can be determined. Devices for measurement of blood flow and blood vessel diameter are well known in the art, and will not be discussed in detail herein.

Theoretically, net blood flow into or out of the brain would require measurement of the blood flow in all veins as well as in all arteries that service blood flow out of and into the cerebral system. In most cases it is, however, possible to model the total blood flow from measurement of blood flow in one vein. With this in mind, we measure (1) the diameter of the vein, and (2) the velocity profile of the venous flow. We calculate a blood volume flow rate in a manner known to those skilled in the art.

The change in the blood volume flow rate is measured at a temporary occlusion of an artery or a vein. One can then calculate a first change in blood volume $\Delta V_1$, which is recorded together with the corresponding change $\Delta p_1$ in ICP, as measured by the previously calibrated pressure responsive measuring device 20, 30.

A second pair of data, $\Delta V_2$ and $\Delta P_2$, is obtained by occluding a different vein or artery. The two pairs of data are inserted into equations (3a) and (3b), and PVI and $P_0$ are then calculated by solving the two equations, e.g. as described above with reference to equations (4)–(8).

After the patient's pressure-volume index PVI and steady state intracranial pressure $P_0$ has been determined, the calibrated measuring device 20, 30, or any other calibrated measurement device responsive to changes in intracranial pressure, can be used to monitor changes in ICP directly and continuously.

Figure 4:
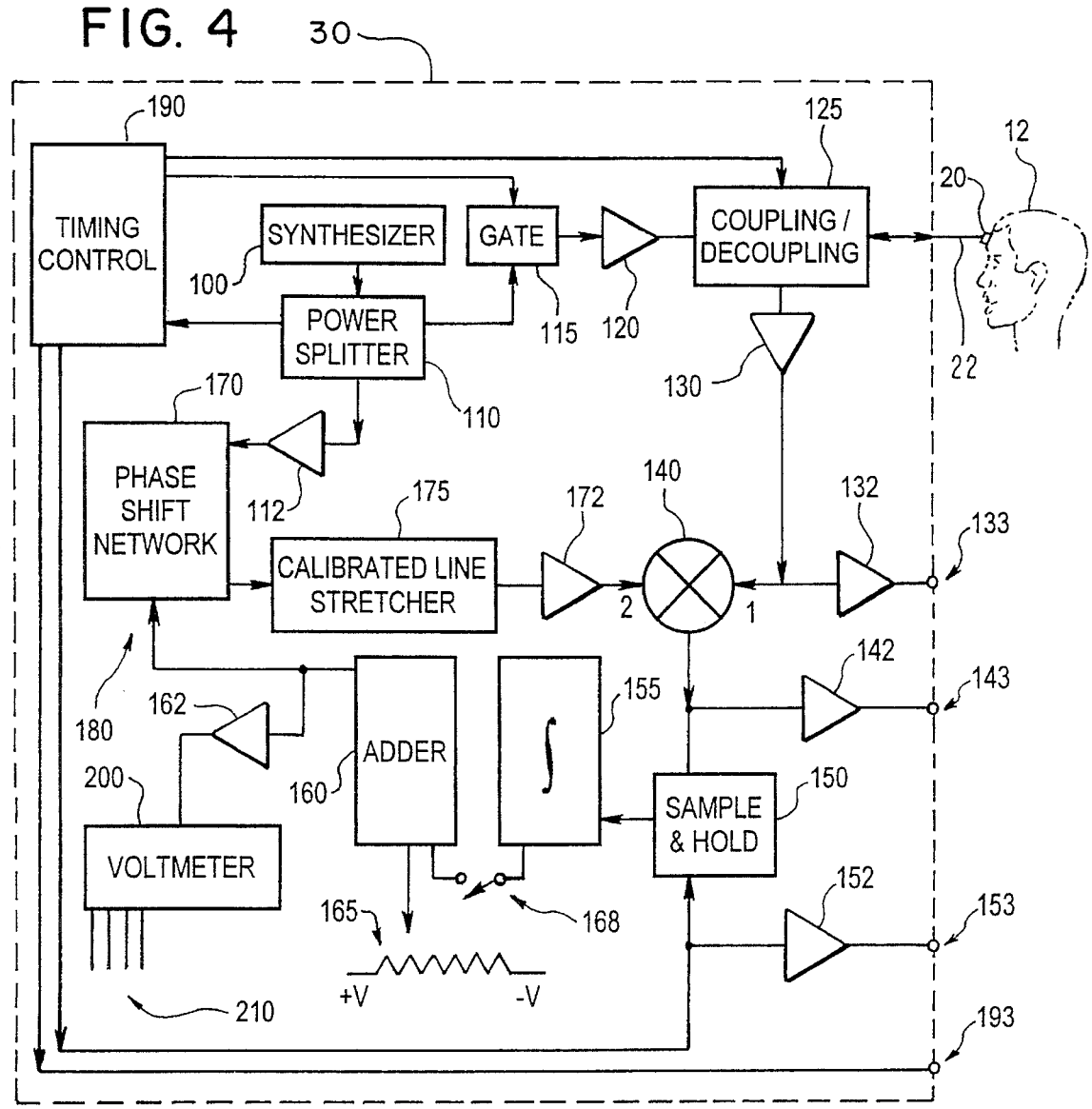
FIG. 4 is a block diagram of a preferred measuring device for use with the invention.

FIG. 4 is a block diagram for a Constant Frequency Pulsed Phase-Locked-Loop (CFPPLL) ultrasonic measurement device, which is a preferred measurement device for use as part of the invention.

The CFPPLL measurement system uses properties of an ultrasonic wave propagating along a path defined by the ultrasonic beam and bound by the skull-meninges-dura complex, or appropriate substructures within this complex, and the measured change in the phase of the propagating ultrasonic wave due to the change in the wave propagation path length accompanying a change in ICP is used as a measure of variations in ICP. The CFPPLL measuring device is preferred because it provides very high sensitivity and excellent repeatability and long term stability.

The CFPPLL measuring device includes an ultrasonic transducer 20, which is shown mounted on the front of the skull 12 of a patient under monitoring. The transducer 20 is via cable 22 supplied with variable width acoustic tonebursts from an electronic apparatus 30, which includes a constant frequency synthesizer 100 followed by a power splitter 110, a gate 115, which determines the width of the acoustic toneburst, a power amplifier 120, and a coupling/decoupling network 125.

Acoustic signals reflected from the far side of the skull 12 is received by the transducer 20 and channelled via the cable 22, the coupling/decoupling network 125, and a preamplifier 130 to a first input (1) of a phase detector 140. A second input (2) of the phase detector 140 receives a second signal from the synthesizer 100 via a power splitter 110, a buffer 112, a voltage controlled phase shift network 170, a calibrated line stretcher 175, and another buffer 172.

The output signal from the phase detector 140 is fed via a sample-and-hold circuit 150 to an integrator 155, and from the integrator 155 via a normally closed phase shift control switch 168 to an adder circuit 160, which also receives a phase set point voltage from a phase set point potentiometer 165. The output from the adder circuit 160 is fed as a control voltage to input 180 of the phase shift network 170, and also to a digital voltmeter 200 used as readout for the measuring device. The digital voltmeter includes an IEEE interface connection 210 for external data storage and processing.

A timing control unit 190 provides all sync and control signals for the gate 115, the coupling/decoupling network 125, and the sample-and-hold circuit 150. The coupling/decoupling network 125 protects the preamplifier 130 from overload by decoupling the preamplifier 130 from the transducer 20 when large voltage drive signals are coupled to the transducer 20, and it improves system sensitivity by decoupling the output of the low-impedance drive amplifier 120 from the transducer 20 when a reflected signal is received by the transducer 20.

The apparatus 30 also provides outputs for supervision and setup, including transducer output 133, phase comparison output 143, control point monitor output 153, and sync signal output 193.

The function of the CFPPLL system outlined above is best understood by considering that a constant frequency signal from an oscillator 100 is split into two signal paths, 1 and 2, and that phase differences between the two signal paths are measured.

Along path 1, which is a measurement path, an acoustic signal generated in transducer 20 traverses the material enclosed by the skull 12 of the patient. The acoustic toneburst travels through the material enclosed by the skull 12, is reflected at the far end of the skull 12, and impinges on the transducer 20 as an echo of the original pulse. Any changes in the propagation conditions, such as path length changes, produce associated phase changes in path 1. These phase changes are the information sought in measurement.

Path 2, which is a reference path, includes a voltage controlled phase shift network 170, whose output is used for phase comparison with the signal from the measurement path (1). The phase detector 140 detects the relative phase difference between the signals in the two paths, and generates an output signal proportional to the cosine of the phase difference. The control voltage to the voltage controlled phase shift network 170 is automatically changed until the output voltage of the phase detector 140 is zero, which occurs when the two signals are in quadrature.

The input to the voltage controlled phase shift network 170 comes through a buffer 112 from the power splitter 110. The buffer 112 provides matching of the electrical input impedance to that of the phase shift network 170. The phase shift is controlled by a dc voltage applied to a control input 181 of the voltage controlled phase shift network 170. The output of the voltage controlled phase shift network 170 passes through a calibrated line stretcher 175, used for calibration of the system, and a buffer 172 to the phase detector 140. During data collection the setting of the calibrated line stretcher 175 is not changed.

Phase comparison of the two paths is performed by the phase detector 140, which is a product detector combined with a low pass filter. The phase detector 140 output voltage can be written as one-half the product of the input voltage amplitudes times the cosine of the phase difference between the two signals. The output of the phase detector 140 is passed both to the sample-and-hold circuit 150, which selects the desired portion of the phase signal, and to an output port 143 through a buffer 142 for observation on an oscilloscope (not shown). The portion of the phase signal chosen for measurement is selected by an adjustable timing pulse to the sample and hold circuit 150, whose output is passed to an integrator 155.

The loop control circuit, which is made up of the sample-and-hold 150, the integrator 155, the phase set point potentiometer 165, and the adder 160, provides the control voltage 180 for the voltage controlled phase shift network 170. The control voltage 180 is a sum of two contributions, one coming from the integrator 155, and the other coming from the phase set point potentiometer 165. The phase set point potentiometer 165 sets the nominal phase shift about which the system operates. The integrator 155 provides a voltage derived from the phase detector 140. When the phase detector 140 output reaches null, the integrator 155 output voltage stabilizes to a constant voltage, and quadrature between paths 1 and 2 are established. The phase shift control switch 168 is closed in the "locked" state when the system is taking a measurement. For setup, it is moved to its open "unlocked" state, so that the voltage controlled phase shift network 170 is under manual control by the phase set point potentiometer 165.

The timing control unit 190 forms all of the necessary timing signals needed by various sections for the measurement application. All timing signals are referenced to the repetition rate, which is determined by counting down from the synthesizer 100. The sync output marks the beginning of the formation of a toneburst and is used for measurement setup and display. An adjustable width of the toneburst is also provided. Signals to the coupling/decoupling network 125 and the sample-and-hold circuit 150, used to measure the phase of the selected portion of the received ultrasonic wave, are controlled by this unit. Timing sequences are adjusted with the aid of an oscilloscope.

Adjustments for measurements are made in the following way:

With the outputs properly connected to an oscilloscope and the phase shift control switch 168 in the open ("unlocked") position, the received tonebursts and the phase comparison voltages are displayed. The frequency of the synthesizer 100 is adjusted so that the amplitudes of the reflected toneburst echoes at output 133 are far out of the noise, and the phase comparison output voltage at output 143 is relatively "flat topped" and stable at that portion of the tone burst echo chosen for measurement. The phase set point potentiometer 165 is adjusted until the phase comparison voltage 180 corresponding to the desired tone burst is approximately 0 V. The control point is adjusted so that the phase signal is sampled well into its latter half. Because of a time delay in the low-pass filter in the phase detector 140 the phase signal is not precisely synchronized with the tonebursts. The phase shift control switch 168 is then placed in its closed ("locked") position for data taking.

A calibration procedure that uses a line stretcher 175 in the reference path (2) permits the conversion of the change in control voltage, monitored by the voltmeter 200, to a change in phase shift between the two paths. Calibration of the voltage controlled phase shift network 170 in a CFPPLL system is normally accomplished by adjusting the calibrated line stretcher 175 to introduce a known phase shift into the calibration path while the system is locked in data taking mode. This results in a change in the phase shift control voltage 180 to the voltage controlled phase shift network 170. The change in phase shift control voltage 180 is recorded, and a change of output voltage for a known phase shift is thus determined. This result is used to calculate changes to the measured phase shifts and, is particularly important information to have in setups requiring measurements of small phase shifts of a few hundred microradians.

When the CFPPLL system is used for measuring and/or monitoring intracranial pressure ICP and pressure-volume index PVI according to the present invention, such absolute calibration of output versus phase angle is not required, but instead the change in output versus change in ICP is calibrated by the tilt angle method or the pressurized skull cap method as described above.

The method described above for non-invasive determination of PVI and ICP according to a preferred embodiment of the invention is not only useful for direct monitoring of ICP, but also for calibration of other measuring devices using indirect methods for non-invasive monitoring of ICP. Such non-invasive measuring devices include, but are not limited to, calipers, head bands, or other devices and measurement systems possessing the sensitivity and accuracy to allow proper calibration, for example, by using the measurement systems to monitor any dimensional changes in the skull or other connected systems, such as the eyeball, inner ear, or anatomical landmarks within or adjacent to the cranial cavity and/or the spine or attached or adjacent structures, or configurational changes of the spine or any other structures responding to increases in intracranial pressure. The invention makes it possible to calibrate such devices so accurate continuous recordings of absolute values of ICP can be obtained without the need for invasive procedures.

Numerous modifications and adaptations of the present invention will be apparent to those skilled in the art. Thus, the following claims and their equivalents are intended to cover all such modifications and adaptations which fall within the true spirit and scope of the present invention.

What is claimed is:

1. A method for non-invasive measurement of intracranial pressure and pressure volume index in a patient, comprising the steps of:
   (a) calibrating a measuring device by introducing known changes in intracranial pressure and reading the corresponding pressure changes with the measuring device;
   (b) inducing known changes in the volume of the cerebrospinal fluid while measuring the corresponding changes in intracranial pressure with the calibrated measuring device;
   (c) obtaining two sets of corresponding values for change in volume and change in intracranial pressure; and
   (d) obtaining values for the pressure volume index and the intracranial pressure for the patient based on the values for change in volume and change in intracranial pressure.

2. A method for non-invasive measurement of intracranial pressure and pressure volume index according to claim 1, wherein said measuring device is an ultrasonic constant frequency pulsed phase-locked-loop measuring device including an ultrasonic transducer applied to the skull of the patient.

3. A method for non-invasive measurement of intracranial pressure and pressure volume index according to claim 1, wherein said known change in intracranial pressure is induced by placing the patient on a tiltable bed and calculating said known change in intracranial pressure from the length of the patient's cerebrospinal system and the tilt angle of the bed.

4. A method for non-invasive measurement of intracranial pressure and pressure volume index according to claim 1, wherein said known change in intracranial pressure is induced by placing an inflatable cap on the patient's skull and inflating said cap to a known pressure.

5. A method for non-invasive measurement of intracranial pressure and pressure volume index according to claim 1, wherein known changes in the volume of the cerebrospinal fluid are induced by injecting boluses of fluid into the spinal cord of the patient.

6. A method for non-invasive measurement of intracranial pressure and pressure volume index according to claim 1, wherein known changes in the volume of the cerebrospinal fluid are induced by temporary obstruction of veins or arteries in the patient's neck while the blood flow into or out of the brain is measured.

7. A method for non-invasive measurement of intracranial pressure and pressure volume index according to claim 1, wherein the step (d) comprises:

obtaining values for the pressure volume index and the intracranial pressure for the patient based on the values for change in volume and change in intracranial pressure using the equation $$\Delta P = P_0(10^{\frac{\Delta V}{PVI}} - 1)$$

where $\Delta P$ is the change in intercranial pressure and $\Delta v$ is the change in volume obtained in step (c).

8. A method for calibrating a device for monitoring changes in intracranial pressure in a patient comprising the steps of:

(a) applying a measuring device to the patient to provide output signals in response to changes in intracranial pressure;

(b) inducing a known change in intracranial pressure by placing the patient on a tiltable bed and calculating said known change in intracranial pressure from the length of the patient's cerebrospinal system and the tilt angle of the bed; and (c) recording an output signal from said measuring device corresponding to said known change in intracranial pressure.

9. A method for calibrating a device for monitoring changes in intracranial pressure in a patient comprising the steps of:

(a) applying a measuring device to the patient to provide output signals in response to changes in intracranial pressure;

(b) inducing a known change in intracranial pressure by placing an inflatable cap on the patient's skull and inflating said cap to a known pressure; and (c) recording an output signal from said measuring device corresponding to said known change in intracranial pressure.

* * * * *